US011084982B2

(12) United States Patent
Meenakshisundaram

(10) Patent No.: US 11,084,982 B2
(45) Date of Patent: Aug. 10, 2021

(54) OPTICALLY TRANSPARENT POLYMERIC ACTUATOR AND DISPLAY APPARATUS EMPLOYING SAME

(71) Applicant: UNIVERSITY OF PITTSBURGH-OF THE COMMONWEALTH SYSTEM OF HIGHER EDUCATION, Pittsburgh, PA (US)

(72) Inventor: Ravi Shankar Meenakshisundaram, Aspinwall, PA (US)

(73) Assignee: University of Pittsburgh-Of the Commonwealth System of Higher Education, Pittsburgh, PA (US)

(*) Notice: Subject to any disclaimer, the term of this patent is extended or adjusted under 35 U.S.C. 154(b) by 37 days.

(21) Appl. No.: 16/306,593

(22) PCT Filed: Jun. 9, 2017

(86) PCT No.: PCT/US2017/036679
§ 371 (c)(1),
(2) Date: Dec. 3, 2018

(87) PCT Pub. No.: WO2017/214469
PCT Pub. Date: Dec. 14, 2017

(65) Prior Publication Data
US 2019/0136133 A1    May 9, 2019

Related U.S. Application Data

(60) Provisional application No. 62/348,525, filed on Jun. 10, 2016.

(51) Int. Cl.
*C09K 19/38* (2006.01)
*C09K 19/02* (2006.01)
(Continued)

(52) U.S. Cl.
CPC .......... *C09K 19/38* (2013.01); *C09K 19/0208* (2013.01); *F03G 7/065* (2013.01); *G06F 3/016* (2013.01); *C09K 2219/03* (2013.01)

(58) Field of Classification Search
CPC ...................................................... C09K 19/38
See application file for complete search history.

(56) References Cited

U.S. PATENT DOCUMENTS

2003/0156099 A1* 8/2003 Yrjanainen ........... G06F 3/0488
345/173
2003/0178609 A1* 9/2003 Hammond-Smith .......................
B42D 25/364
252/587

(Continued)

OTHER PUBLICATIONS

M. R. Shankar, M. L. Smith, V. P. Tondiglia, K. M. Lee, M. E. McConney, D. H. Wang, L-S. Tan, T. J. White, "Contactless, Photoinitiated Snap-through in Azobenzene-functionalized Polymers," Proceedings of the National Academy of Sciences, vol. 110, pp. 18792-18797, 2013.

*Primary Examiner* — Sang V Nguyen
(74) *Attorney, Agent, or Firm* — Philip E. Levy; Eckert Seamans Cherin & Mellott, LLC

(57) ABSTRACT

An optically transparent actuator apparatus is provided that includes an optically transparent bi-stable member including an optically transparent liquid crystalline polymer layer. The bi-stable member is structured to move from a first state to a second state in response to a first stimulus and from the second state to the first state in response to a second stimulus. Also, a display apparatus includes a plate member and an actuator assembly coupled to the plate member. The actuator assembly includes a number of optically transparent liquid crystalline polymer layers, wherein each of the opti-
(Continued)

cally transparent liquid crystalline polymer layers is structured to move from a first state to a second state in response to a first stimulus.

20 Claims, 6 Drawing Sheets

(51) Int. Cl.
*F03G 7/06* (2006.01)
*G06F 3/01* (2006.01)

(56) References Cited

U.S. PATENT DOCUMENTS

| | | | | |
|---|---|---|---|---|
| 2007/0237906 | A1* | 10/2007 | Li | G02F 1/1334 |
| | | | | 428/1.2 |
| 2014/0375465 | A1* | 12/2014 | Fenuccio | A61B 5/11 |
| | | | | 340/691.1 |
| 2019/0050102 | A1* | 2/2019 | Johnson | H01L 41/1132 |

* cited by examiner

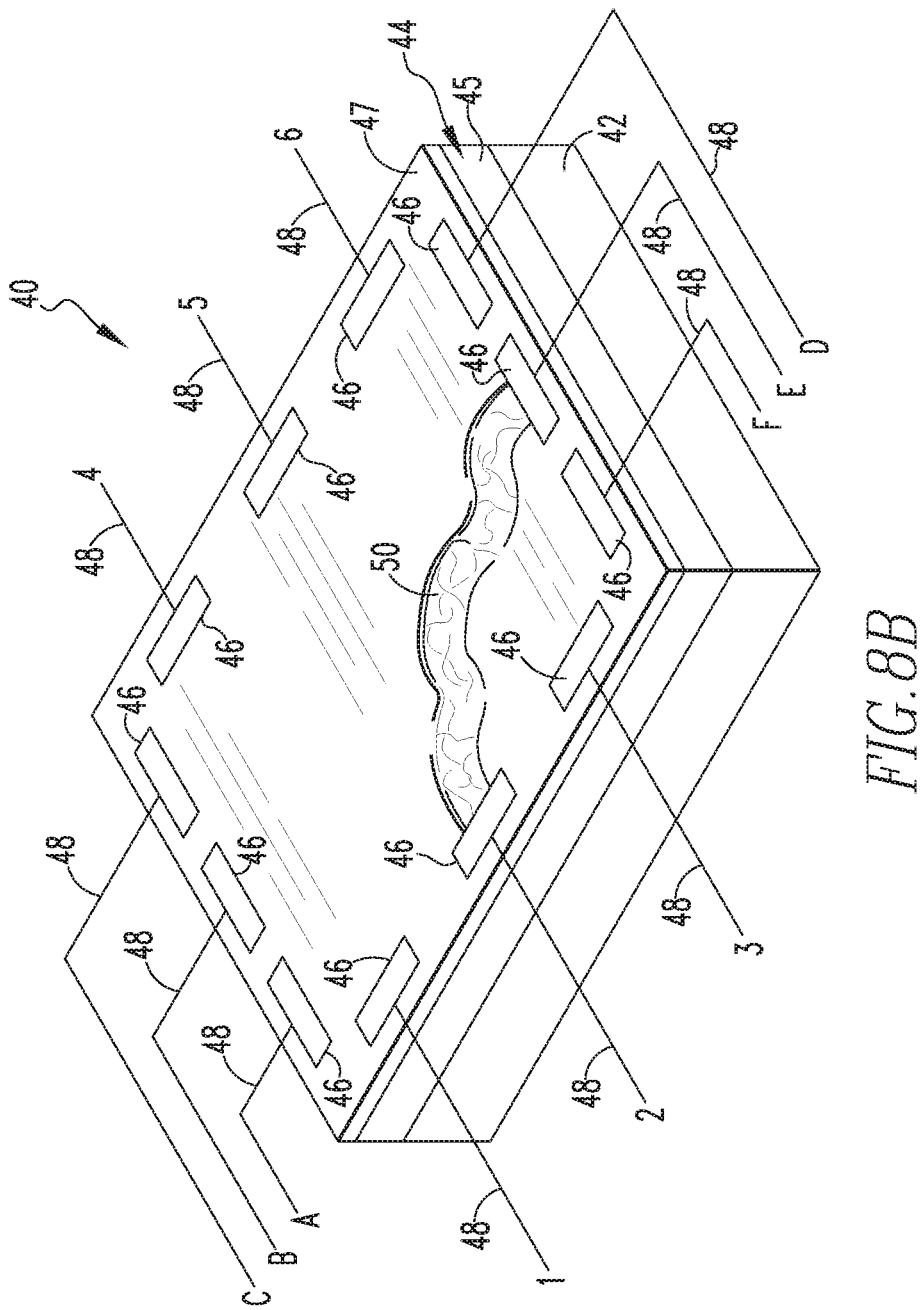

OPTICALLY TRANSPARENT POLYMERIC ACTUATOR AND DISPLAY APPARATUS EMPLOYING SAME

CROSS-REFERENCE TO RELATED APPLICATIONS

This application is a U.S. National Stage Application under 35 U.S.C. § 371 of PCT International Application No. PCT/US2017/036679, entitled "Optically Transparent Polymeric Actuator and Display Apparatus Employing Same," filed on Jun. 9, 2017, which claims priority under 35 U.S.C. § 119(e) from U.S. provisional patent application No. 62/348,525, entitled "Optically Transparent Active Surfaces for Vivid Displays with Haptic Feedback," filed on Jun. 10, 2016, the contents of which are incorporated herein by reference.

GOVERNMENT CONTRACT

This invention was made with government support under grant #1435489 awarded by the National Science Foundation (NSF) and grant #FA9550-14-1-0229 awarded by the United States Air Force/Air Force Office of Scientific Research (USAF/AFOSR). The government has certain rights in the invention.

BACKGROUND OF THE INVENTION

1. Field of the Invention

The present invention relates to actuator devices and displays that employ such devices, and, in particular, to an optically transparent polymeric actuator and display devices employing same, such as display devices structured to provide haptic feedback and/or to deform to provide three-dimensional (3D) structures as needed.

2. Description of the Related Art

Eliciting a programmed mechanical response to a non-mechanical stimulus has underpinned the development of shape memory materials in metals, ceramics and polymers. In low-density polymeric materials, the ability to elicit shape changes in response to magnetic, electric, photonic and chemical stimulus holds implications for the fabrication of adaptive machines with applications in the biomedical, electronics and defense sectors. In polymers, the shape memory can be stored via an array of molecular mechanisms including crystallization/vitrification in covalently cross-linked networks, by phase segregation in physically cross-linked block copolymers, and by programming rigid molecular segments in liquid crystalline polymers. Eliciting a memorized shape is often pursued using heat and finds implementation in an array of products involving heat-shrink polymers. In addition, a range of other triggers have been examined, including electrical fields, magnetic fields, UV, and IR irradiation.

A significant challenge in the development of active surfaces that integrate with wearable electronics and smart devices is the challenge of achieving the combination of broad wavelength optical transmission, mechanical adaptivity that is ultrafast, low energy consumption and the encapsulation of the structures in small form factors. This eliminates a vast number of existing actuator technologies from being utilized seamlessly in such applications.

SUMMARY OF THE INVENTION

In one embodiment, an optically transparent actuator apparatus is provided that includes an optically transparent bi-stable member including an optically transparent liquid crystalline polymer layer. The bi-stable member is structured to move from a first state to a second state in response to a first stimulus and from the second state to the first state in response to a second stimulus.

In another embodiment, a method of controlling an actuator in a display apparatus is provided. The method includes providing a first stimulus to an optically transparent bi-stable member including an optically transparent liquid crystalline polymer layer to cause the bi-stable member to move from a first state to a second state, and providing a second stimulus to the bi-stable member to cause the bi-stable member to move from the second state to the first state.

In still another embodiment, a display apparatus is provided that includes a plate member and an actuator assembly coupled to the plate member. The actuator assembly includes a number of optically transparent liquid crystalline polymer layers, wherein each of the optically transparent liquid crystalline polymer layers is structured to move from a first state to a second state in response to a first stimulus.

In yet another embodiment, a method of making an optically transparent actuator element is provided. The method includes forming a first structure including: (i) forming an optically transparent liquid crystalline polymer layer, and (ii) forming a first optically transparent conductor member on a first surface of the optically transparent liquid crystalline polymer layer and a second optically transparent conductor member on a first surface of the optically transparent liquid crystalline polymer layer. The method further includes applying a number of displacement forces to one or more ends of the first structure to cause the first structure to buckle and provide an arch-shaped portion in the first structure.

BRIEF DESCRIPTION OF THE DRAWINGS

FIGS. 8A and 8B are schematic diagrams of a display assembly according to an alternative exemplary embodiment of the disclosed concept.

DETAILED DESCRIPTION OF EXEMPLARY EMBODIMENTS

Figure 1A:
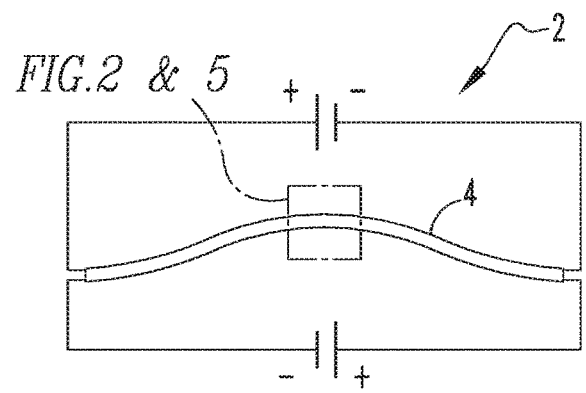
FIGS. 1A and 1B show an optically transparent actuator element according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the statement that two or more parts or components "engage" one another shall mean that the parts exert a force against one another either directly or through one or more intermediate parts or components.

As used herein, the term "number" shall mean one or an integer greater than one (i.e., a plurality).

As used herein, the term "arch-shaped" shall mean a number of curved, folded, creased or wrinkled shapes that spans a space from a first point to a second point, and shall include both symmetrical and non-symmetrical curved shapes.

As used herein, the term "cross linked" shall mean conversion of monomer mixtures into cured, solid polymer films following exposure to heat and or light.

As used herein, the term "optically transparent" shall mean allowing transmission of light in the part of the electromagnetic spectrum that is visible to the human eye (typically wavelengths of light ranging from 350 nm to 800 nm).

As used herein, the term "liquid crystalline polymer" shall mean a cross linked polymer created from liquid crystalline monomers, wherein the monomers possess a mesogenic/nematic core which can develop orientational order across macroscopic lengths-scales, and shall include, without limitation, cross linked films that have twisted nematic and splayed liquid crystalline ordering.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in detail herein, the disclosed concept provides an optically transparent actuator that may be structured to implement an optically transparent display, such as a display that provides haptic feedback and/or generated 3D structures on command. The disclosed concept is described herein, for purposes of explanation, in connection with numerous specific details in order to provide a thorough understanding of the disclosed subject matter. It will be evident, however, that the disclosed concept can be practiced without these specific details without departing from the spirit and scope of this innovation.

Figure 1B:
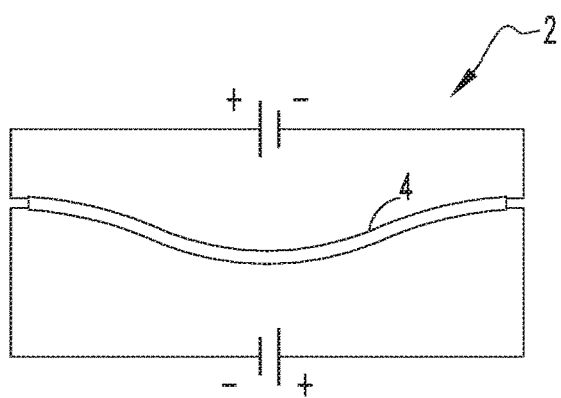

FIGS. 1A and 1B show an optically transparent actuator element 2 according to an exemplary embodiment of the disclosed concept. As seen in FIGS. 1A and 1B, actuator element 2 includes a bi-stable arch member 4 structured to move from a first stable state (shown in FIG. 1A) to a second stable state (shown in FIG. 1B) in response to a first stimulus being applied thereto, and from the second stable state (FIG. 1B) to the first stable state (FIG. 1A) in response to a second stimulus being applied thereto. In the illustrated exemplary embodiment described herein and shown schematically in FIGS. 1A and 1B, the first stimulus and the second stimulus take the form of heat that is selectively applied to bi-stable arch member 4 by way of resistive heating (also known as Joule heating or ohmic heating). In particular, as shown schematically in FIG. 1A and FIG. 1B, an electric current is passed through a conductor forming part of bi-stable arch member 4 to generate the heat. In the exemplary embodiment, the required voltages are on the order of 1V to 10V and the current loads are approximately 10 mA. This is very different from known dielectric actuators which require hundreds or thousands of volts to operate. In addition, in the exemplary embodiment, the movement from the first stable state to the second stable state and the movement from the second stable state to the first stable state is by snap-through action of the arch-shaped member.

In exemplary embodiments of the disclosed concept, described in greater detail elsewhere herein, a number of transparent actuator elements 2 may be used to form a haptic or 3D pop-up display. In such implementations, each bi-stable arch member 4 is structured to: (i) not impact/engage an optically transparent plate member when in the first state, and (ii) impact/engage the optically transparent plate member and thereby provide haptic feedback and/or a three-dimensional shape when in the second state. In the case of the haptic display implementation, when the transparent actuator element 2 impacts the optically transparent plate member at the end of its snap-through, it transmits an impulse through the optically transparent plate member to provide haptic feedback. In the case of the 3-D pop-display implementation, the transparent actuator element to impacts the optically transparent plate member at the end of its snap through, it deforms the optically transparent plate member to form part of a three-dimensional shape. It will be appreciated that still other applications of the transparent actuator element 2 are possible within the scope of the disclosed concept.

Figure 2:
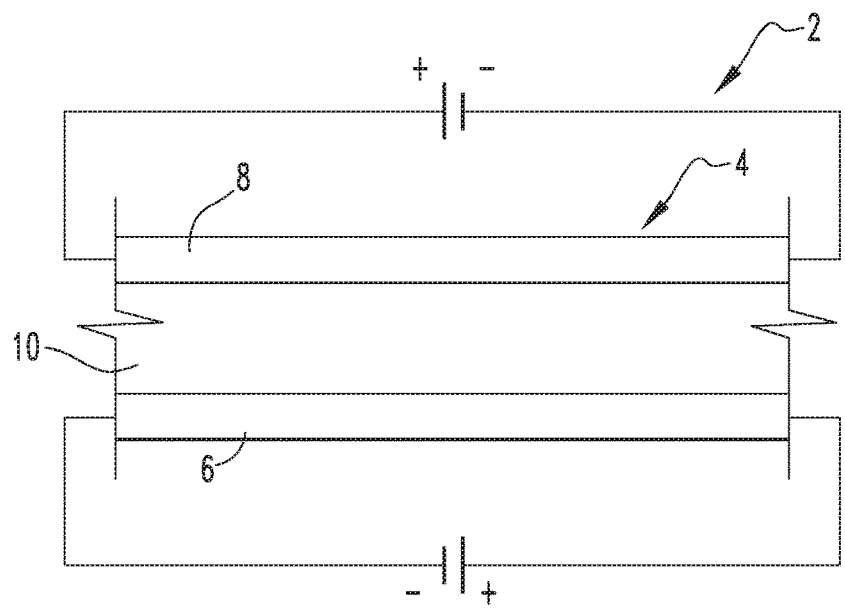
FIG. 2 is a schematic diagram of a portion of an optically transparent actuator element according to the exemplary embodiment.

FIG. 2 is a schematic diagram of a portion (See FIG. 1A) of transparent actuator element 2 according to the exemplary embodiment. As seen in FIG. 2, bi-stable arch member 4 is a multilayer structure. In particular, bi-stable arch member 4 in the illustrated exemplary embodiment includes a bottom optically transparent conductor member 6 and a top optically transparent conductor member 8. In the exemplary embodiment, bottom optically transparent conductor member 6 and top optically transparent conductor member 8 are both made of a transparent conductive material such as, without limitation, indium tin oxide (ITO). Alternatively, bottom optically transparent conductor member 6 and top optically transparent conductor member 8 may be made of other optically transparent materials such as graphene, nanostructured transparent conductors, metallic ink-based transparent conductors or carbon nanotube (CNT) conductors. In addition, bi-stable arch member 4 includes a liquid crystalline polymer layer 10 provided between bottom optically transparent conductor member 6 and top optically transparent conductor member 8.

When bi-stable arch member 4 is in a downward state as illustrated in FIG. 1B, it can be toggled to snap upward to an upward state when top optically transparent conductor number 8 is energized and thereby generates heat resistively. When bi-stable arch member 4 is in the upward state as illustrated in FIG. 1A, it can be toggled to snap downward to the downward state when bottom optically transparent conductor member 6 is energized and thereby generates heat resistively. Thus, repetitive actuation of bi-stable arch member 4 is possible.

In the exemplary embodiment, liquid crystalline polymer layer 10 includes a number of liquid crystalline polymer films. For example, and without limitation, liquid crystalline polymer layer 10 may include a number of twisted nematic liquid crystalline polymer films 12 as shown schematically in FIG. 3, or a number of splayed liquid crystalline polymer films 18 as shown schematically in FIG. 4.

Figure 3:
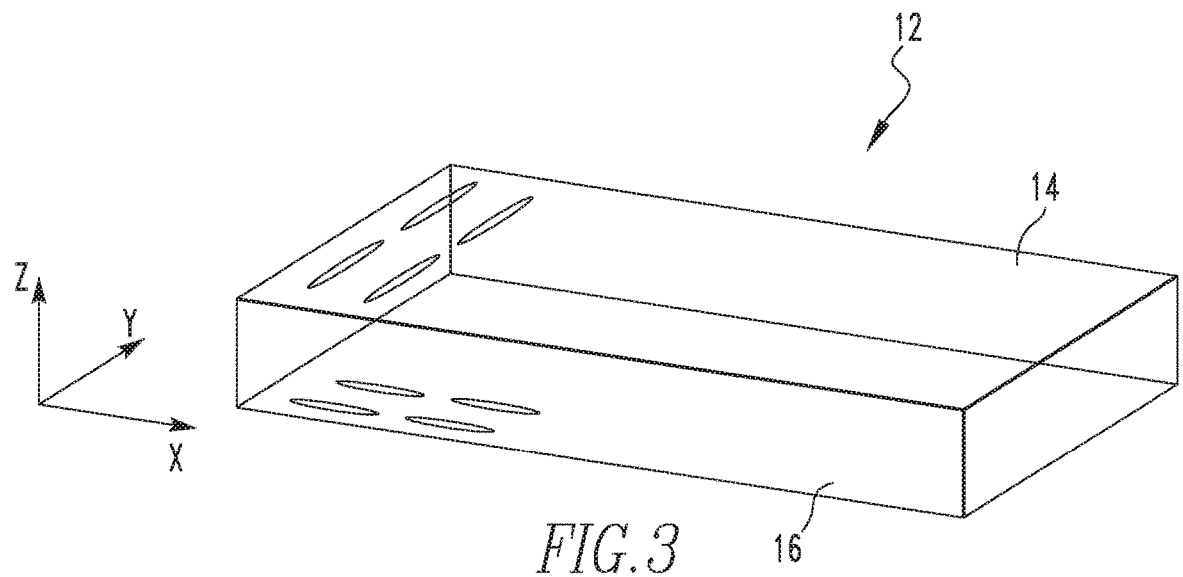
FIG. 3 is a schematic diagram of a twisted nematic liquid crystalline polymer film employed in one embodiment of the disclosed concept.

Referring to FIG. 3, as is known in the art, twisted nematic liquid crystalline polymer film 12 includes a top planar aligned side 14 wherein the molecules are aligned in a first planar manner, and a bottom plane aligned side 16 wherein the molecules are aligned in a second planar manner. As illustrated in FIG. 3, the molecules are aligned orthogonally on each side. In particular, in top planar aligned side 14, the molecules are aligned along the short axis, and in bottom planar aligned side 16, the molecules are aligned along the long axis (this could, of course, be reversed with the molecules aligned along the short axis being on the bottom and molecules aligned along the long axis being on the top). In both top planar aligned side 14 and bottom planar aligned side 16, the molecular axis is in the plane of the respective surface.

Figure 4:
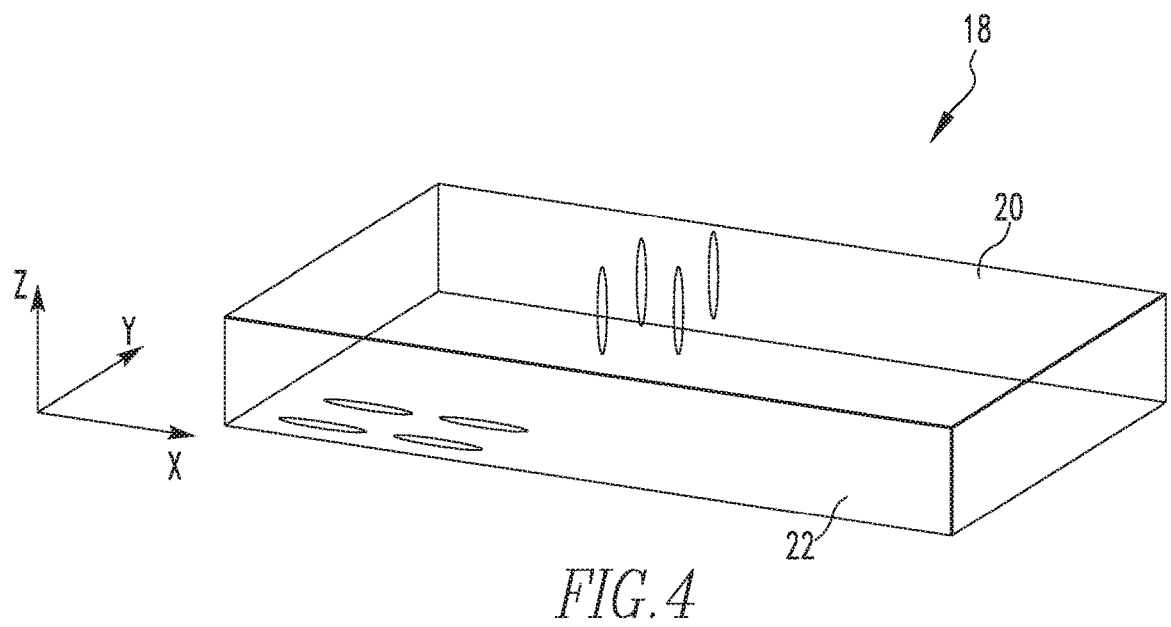
FIG. 4 is a schematic diagram of a splayed liquid crystalline polymer film employed in another embodiment of the disclosed concept.

Referring to FIG. 4, as is known in the art, splayed liquid crystalline polymer film 18 includes a homeotropic side 20 and a planar aligned side 22. In homeotropic side 20, the molecules are aligned vertically (homeotropically), while in planar aligned side 22, the molecules are aligned in a planar manner in the plane of the surface. More specifically, as seen in FIG. 4, in homeotropic side 20, the molecules are perpendicular to the surface of homeotropic side 20, and in planar aligned side 22, the molecules are aligned along the long axis (alternatively, the molecules could be aligned along the short axis).

Figure 5:
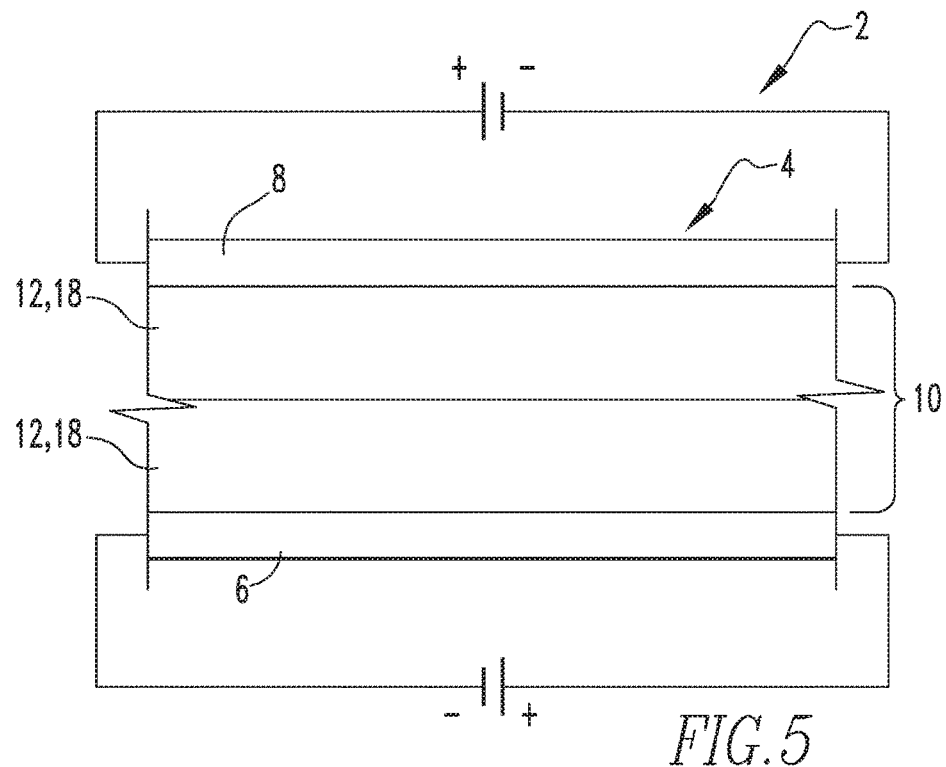
FIG. 5 is a schematic diagram of a portion of a transparent actuator element according to one particular non-limiting exemplary embodiment of the disclosed concept.

FIG. 5 is a schematic diagram of a portion (See FIG. 1A) of transparent actuator element 2 according to one particular, non-limiting exemplary embodiment. As seen in FIG. 5, liquid crystalline polymer layer 10 includes two cross-linked films that are bonded to one another. For example, the two cross-linked films may be two cross-linked twisted nematic liquid crystalline polymer films 12 as shown in FIG. 3 or two cross-linked splayed liquid crystalline polymer films 18 as shown in FIG. 4. In one particular implementation, the two cross-linked films are two cross-linked twisted nematic liquid crystalline polymer films 12 having the top planar aligned sides 14 thereof bonded together face to face. In another particular implementation, the two cross-linked films are two splayed liquid crystalline polymer films 18 having the homeotropic sides 20 thereof bonded together face-to-face. In this particular exemplary embodiment, it is desirable to use a right-handed chiral dopant, which ensures the same sense of rotation of the director through the thickness in each film.

In an another particular implementation, liquid crystalline polymer layer 10 comprises an integral sample that has a supertwisted nematic configuration. In this configuration, liquid crystalline polymer layer 10 comprises an integral film where the nematic director undergoes a complete period of rotation through the thickness. This configuration will function essentially the same as the bonded configuration described above, but it can be a single integral film instead of making two and bonding them face to face as described.

In addition, in the exemplary embodiment, each film of liquid crystalline polymer layer 10 is on the order of 10 µm to 500 µm in thickness. Also, the optically transparent conductor members 6 and 8 are each on the order of tens of nanometers in thickness.

According to one non-limiting, exemplary embodiment, a plurality of bi-stable arch members 4 as shown in FIG. 5 may be formed in the following manner. First, a mixture comprising an acrylate-functionalized mesogen with trace amounts of chiral dopant and trace amounts of Irgacure 784 is capillary filled in patterned glass cells to create a sheet of material. A plurality of strips each forming an individual liquid crystalline polymer films 12 and/or 18 are then be created by excising such strips from the sheet of material. The harvested strips are then adhered together (e.g., glued together) with suitable orientations as described herein to create the sandwich structure of liquid crystalline polymer layer 10 shown in FIG. 5. Thereafter, a suitable deposition technique, such as RF magnetron sputtering, e-beam deposition, atomic layer deposition or transfer printing, is be used to deposit bottom optically transparent conductor member 6 and top optically transparent conductor member 8 (e.g., made from ITO, graphene, CNT, nanowire arrays, nanomesh structures) onto each side of the strips as shown in FIG. 5. Next, the strip-shaped (non-arched) samples as just formed are held at the terminal ends thereof (e.g., by being mounted in rigid supports), and a displacement force is applied at each end (inwardly toward the center) to create an arch-shape (bi-stable) by buckling.

Figure 6:
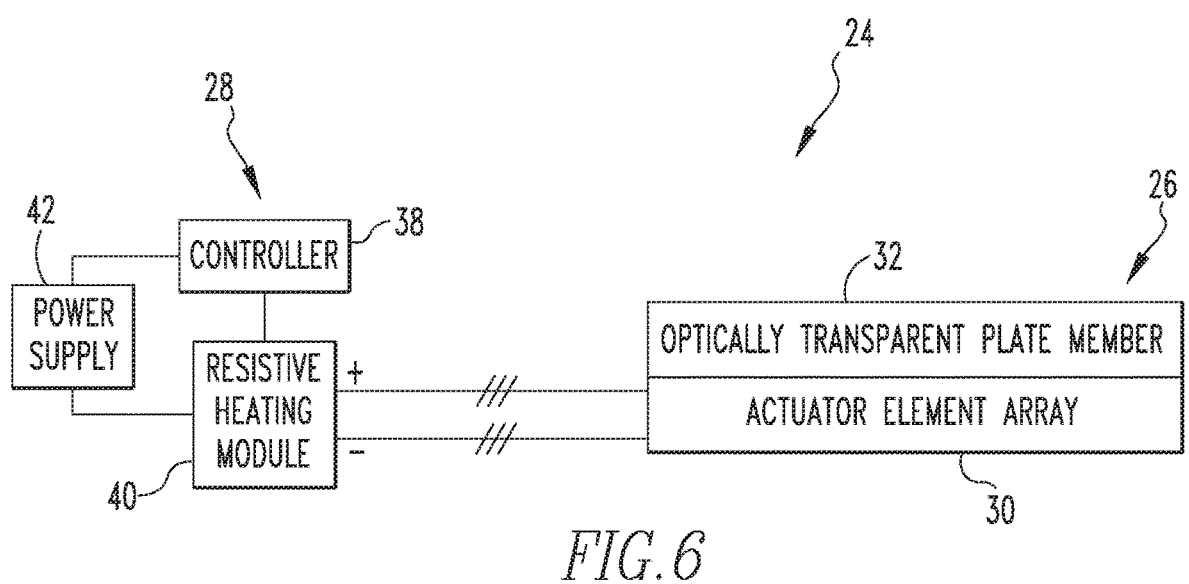
FIG. 6 is a schematic diagram of a display apparatus according to an exemplary embodiment of the disclosed concept.

FIG. 6 is a schematic diagram of a display apparatus 24 according to another exemplary embodiment of the disclosed concept. In the illustrated exemplary embodiment, display apparatus 24 is a haptic display apparatus that provides location sensitive haptic feedback using transparent actuator elements 2 as described herein.

Figure 7:
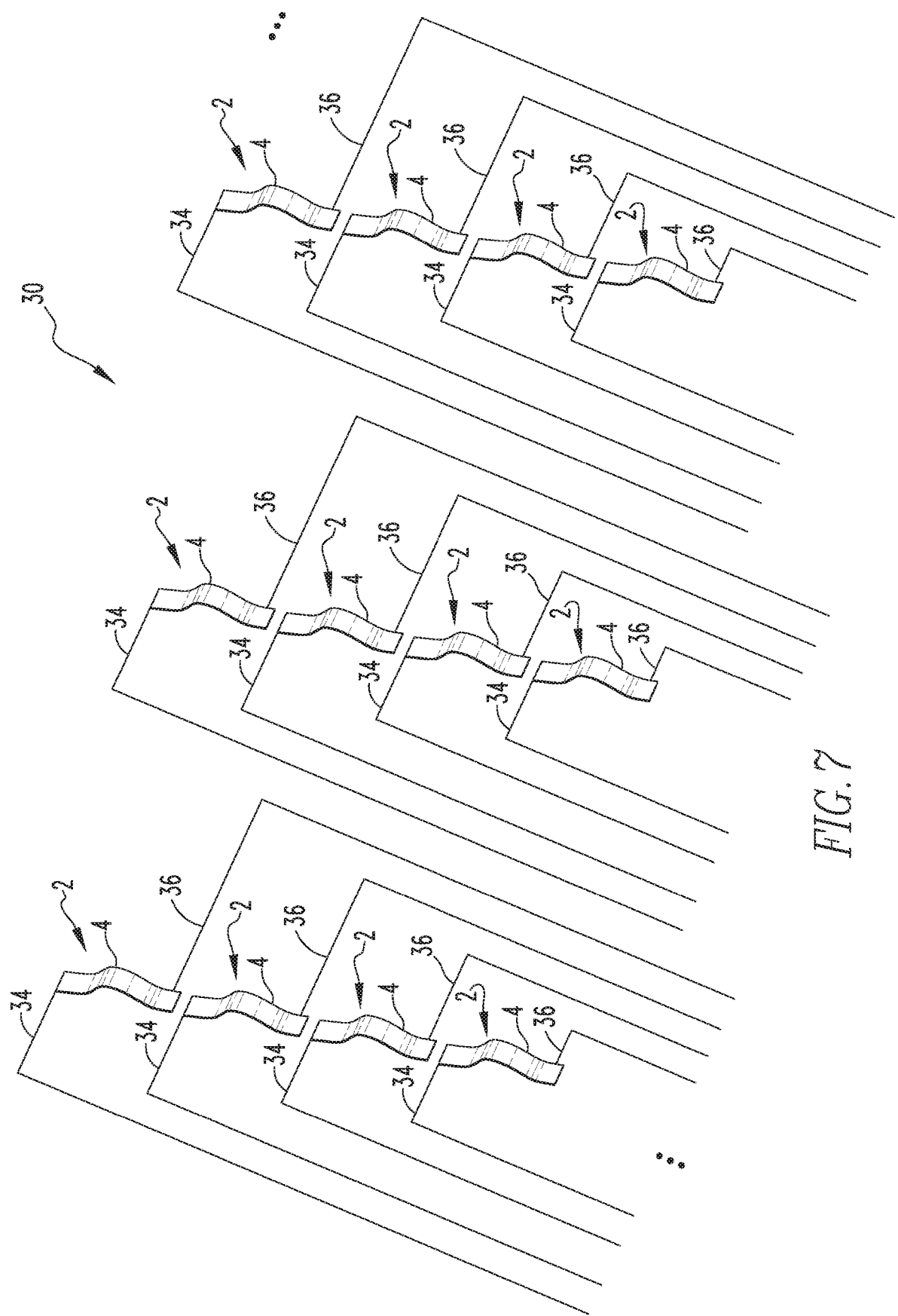
FIG. 7 is a schematic diagram of an actuator element array according to one particular exemplary embodiment of the disclosed concept.

In particular, as seen in FIG. 6, display apparatus 24 includes a display assembly 26 that is coupled to an electronic control system 28. Display assembly 26 includes an actuator element array 30 that is operatively coupled to an optically transparent plate member 32. Actuator element array 30 according to one particular exemplary embodiment is shown in FIG. 7. As seen in FIG. 7, actuator element array 30 includes a plurality of transparent actuator elements 2 arranged in an array pattern including a plurality of rows and a plurality of columns. In the illustrated exemplary embodiment, three rows and four columns are shown. It will be understood, however, that that is meant to be exemplary only, and that more or less rows and/or columns may be employed within the scope of the disclosed concept. Each transparent actuator element 2 in actuator element array 30 is individually addressable/accessible by way of wire (conductor) members 34 and wire (conductor) members 36. In this manner, electrical current may be selectively and individually provided to the bottom optically transparent conductor members 6 and the top optically transparent conductor members 8 of the individually actuator elements 2 as desired in order to actuate each individual transparent actuator element 2 in the manner described herein. In the exemplary embodiment, wire members 34 are coupled to the bottom optically transparent conductor members 6 and wire members 36 are coupled to the top optically transparent conductor members 8.

Optically transparent plate member 32 is, in the exemplary embodiment, a glass, ceramic, or polymer plate. When any transparent actuator element 2 is actuated and thereby impacts optically transparent plate member 32 at the end of its snap-through, it transmits an impulse through optically transparent plate member 32 to provide haptic feedback.

Display assembly 26 is operatively coupled to and controlled by electronic control system 28. Electronic control system 28 includes a controller 38, a resistive heating module 40, and a power supply 42. Controller 38 may be any suitable processing device such as, without limitation, a microprocessor, a microcontroller, or an application specific integrated circuit. Resistive heating module 40 is structured and configured to provide a low current (on the order of tens of mA) with a low voltage (on the order of 1V to 10V) selectively to one or more of the wire members 34 and/or 36 as desired in order to selectively control the actuation of the bi-stable arch members 6 of the transparent actuator elements 2 between the first and second states thereof as described herein. Thus, as just described, display apparatus 24 provides a display surface that is able to provide location sensitive haptic feedback.

In an alternative embodiment, display apparatus 24 may be provided with a deformable/morphable display surface which can be made to deform using low-power as described herein. In particular, in such an implementation, optically transparent plate member 32 would be made of a deformable transparent material such as, without limitation, a liquid crystalline polymer or a shape memory polymer, among others, either as integral films or those attached or suspended on a suitable substrate. In such a configuration, actuation of the transparent actuator elements 2 as described herein would cause selected portions of the deformable optically transparent plate member 32 to be deformed so as to project 3-D shapes on command. In such an implementation, display apparatus 24 may be used to provide a 3D pop-up display for use on a device such as, without limitation, a hand-held device like a smartphone.

Figure 8A:
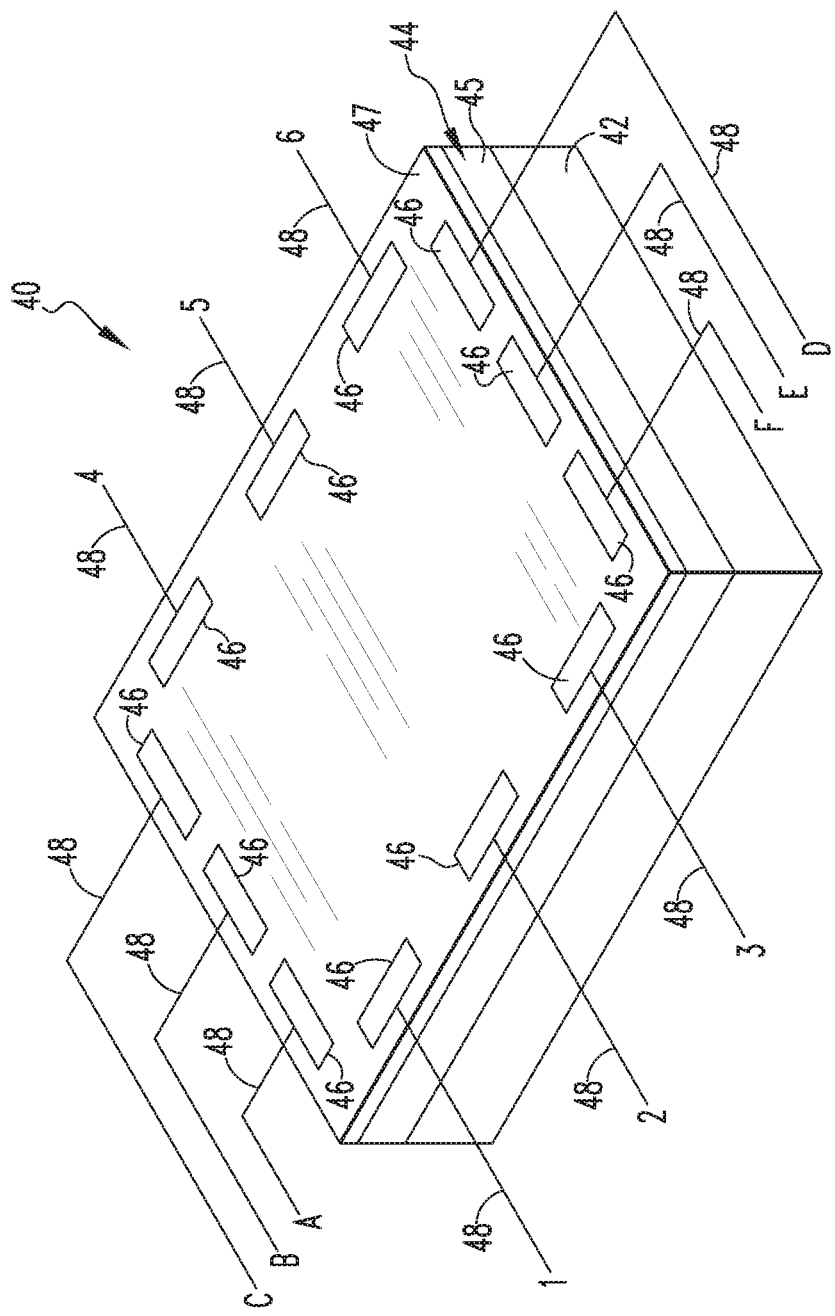

FIGS. 8A and 8B are schematic diagrams of a display assembly 40 according to an alternative exemplary embodiment that may be coupled to an electronic control system such as electronic control system 28 shown in FIG. 6. As described in detail below, display assembly 40 includes a continuous liquid crystalline polymer film structure on which electrodes are provided. The electrodes are structured to be powered in pairs, which powering would cause a portion of the continuous liquid crystalline polymer film structure to wrinkle and thereby create ripples which may be used to provide haptic feedback and/or generate three-dimensional shape as described herein. In particular, referring to FIG. 8A, display assembly 40 includes a substrate 42 and a liquid crystalline polymer film structure 44 provided on a top surface of substrate 42. Substrate 42 may be, for example without limitation, a gel, a soft oligomer, a soft polymer like polydimethylsiloxane (PDMS), or simply air. Liquid crystalline polymer film structure 44 includes a liquid crystalline polymer film layer 45 that is similar to liquid crystalline polymer film 10 described herein (which may include a number of twisted nematic liquid crystalline polymer films 12 as shown schematically in FIG. 3, or a number of splayed liquid crystalline polymer films 18 as shown schematically in FIG. 4) and one or more optically transparent conductor layers 47 (similar to optically transparent conductor members 6 and 8 described herein) coupled to the liquid crystalline polymer film layer 45. As seen in FIG. 8A, a plurality of conductive electrodes 46 are provided on the top surface of liquid crystalline polymer film structure 44. In the exemplary embodiment, each electrode 46 is a transparent conductor as described elsewhere herein and is electrically coupled to optically transparent conductive layer 47. In addition, each electrode 46, labeled 1-6 and A-F, is coupled to a resistive heating module such as resistive heating module 40 of electronic control system 28, by an associated conductor 48 which allows current to be selectively and individually provided to each electrode 46.

In operation, when current is applied between pairs of electrodes 46, the region of liquid crystalline polymer film structure 44 between the pairs of electrodes 46 is heated by the current, which actuates liquid crystalline polymer film structure 44 (e.g., the twisted nematic or the splayed liquid crystalline polymer of liquid crystalline polymer film layer 45). This is shown, for example, in FIG. 8B, wherein current is applied to the electrodes 46 labeled 2 and E, which results in ripples 50 being provided in the region between those two electrodes. The reason liquid crystal polymer film structure 44 wrinkles is due to a buckling transition that is very similar to what occurs in actuator elements 2 described elsewhere herein. Basically, if a thin liquid crystalline polymer film, like that in liquid crystalline polymer film structure 44, is subjected to compressive strains, here generated using electric heating, it will buckle. If the film is a continuous film, like that in liquid crystalline polymer film structure 44, the buckling will result in a wrinkled/rippled pattern. When the current is turned off, the film relaxes, the strains are removed and the buckled pattern goes away. In one particular embodiment, an optically transparent plate member 32 as shown in FIG. 6 is provided on top of liquid crystalline polymer film 44 and electrodes 46.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An optically transparent actuator apparatus, comprising:
    an optically transparent bi-stable member including an optically transparent liquid crystalline polymer layer, wherein the bi-stable member is structured to move from a first state to a second state in response to a first stimulus and from the second state to the first state in response to a second stimulus, wherein the bi-stable member has an arch-shaped portion, wherein the first state is a first arched state and the second state is a second arched state opposite the first arched state, and wherein the movement from the first state to the second state and the movement from the second state to the first state is each by snap-through action so as to provide haptic feedback.

2. The actuator apparatus according to claim 1, wherein the liquid crystalline polymer layer comprises a number of twisted nematic liquid crystalline polymer films.

3. The actuator apparatus according to claim 2, wherein the liquid crystalline polymer layer comprises a pair of cross-linked twisted nematic liquid crystalline polymer films.

4. The actuator apparatus according to claim 1, wherein the liquid crystalline polymer layer comprises a number of splayed liquid crystalline polymer films.

5. The actuator apparatus according to claim 4, wherein the liquid crystalline polymer layer comprises a pair of cross-linked splayed liquid crystalline polymer films.

6. The actuator apparatus according to claim 1, wherein the bi-stable member comprises a layered structure including: (i) a first transparent conductor layer, (ii) a second transparent conductor layer, and (iii) the liquid crystalline polymer layer, wherein the liquid crystalline polymer layer is provided in between the first transparent conductor and the second transparent conductor.

7. The actuator apparatus according to claim 6, wherein the first transparent conductor and the second transparent conductor are each an indium tin oxide transparent conductor, a graphene transparent conductor, a nanostructured transparent conductor, a metallic ink-based transparent conductor, or a carbon nanotube transparent conductor.

8. The actuator apparatus according to claim 1, wherein the first stimulus and the second stimulus are each heat.

9. A method of controlling an actuator in a display apparatus to provide haptic feedback, comprising:
providing a first stimulus to an optically transparent bi-stable member including an optically transparent liquid crystalline polymer layer to cause the bi-stable member to move from a first state to a second state; and
providing a second stimulus to the bi-stable member to cause the bi-stable member to move from the second state to the first state, wherein the bi-stable member has an arch-shaped portion, wherein the first state is a first arched state and the second state is a second arched state opposite the first arched state, and wherein the movement from the first state to the second state and the movement from the second state to the first date is each by snap-through action.

10. The method according to claim 9, wherein the first stimulus and the second stimulus are each heat.

11. The actuator apparatus according to claim 1, wherein the liquid crystalline polymer layer comprises a first side wherein the molecules in the first side are aligned in a first manner, and a second side wherein the molecules in the second side are aligned in a second manner that is orthogonal to the first manner.

12. The actuator apparatus according to claim 11, wherein first side is a first planar aligned side wherein the molecules in the first planar aligned side are aligned in a first planar manner, and wherein the second side is a second planar aligned side wherein the molecules in the second planar aligned side are aligned in a second planar manner that is orthogonal to the first planar manner.

13. The actuator apparatus according to claim 12, wherein the molecules in the first planar aligned side are aligned along a first axis of the optically transparent bi-stable member and the molecules in the second planar aligned side are aligned along a second axis of the optically transparent bi-stable member that is orthogonal to the first axis.

14. The actuator apparatus according to claim 13, wherein the first axis is a short axis of the optically transparent bi-stable member and the second axis is a long axis of the optically transparent bi-stable member.

15. The actuator apparatus according to claim 11, wherein first side is a first planar aligned side wherein the molecules in the first planar aligned side are aligned in a first planar manner, and wherein the molecules in the second side are aligned homeotropically.

16. The method according to claim 9, wherein the liquid crystalline polymer layer comprises a first side wherein the molecules in the first side are aligned in a first manner, and a second side wherein the molecules in the second side are aligned in a second manner that is orthogonal to the first manner.

17. The method according to claim 16, wherein the first side is a first planar aligned side wherein the molecules in the first planar aligned side are aligned in a first planar manner, and wherein the second side is a second planar aligned side wherein the molecules in the second planar aligned side are aligned in a second planar manner that is orthogonal to the first planar manner.

18. The method according to claim 17, wherein the molecules in the first planar aligned side are aligned along a first axis of the optically transparent bi-stable member and the molecules in the second planar aligned side are aligned along a second axis of the optically transparent bi-stable member that is orthogonal to the first axis.

19. The method according to claim 18, wherein the first axis is a short axis of the optically transparent bi-stable member and the second axis is a long axis of the optically transparent bi-stable member.

20. The method according to claim 16, wherein the first side is a first planar aligned side wherein the molecules in the first planar aligned side are aligned in a first planar manner, and wherein the molecules in the second side are aligned homeotropically.

* * * * *